United States Patent [19]

Gourse

[11] 4,299,615
[45] Nov. 10, 1981

[54] METHOD OF INCREASING THE YIELDS OF SUGAR CANE WITH PHOSPHONIC ACIDS

[75] Inventor: Jerome A. Gourse, Skokie, Ill.

[73] Assignee: Velsicol Chemical Corporation, Chicago, Ill.

[21] Appl. No.: 105,343

[22] Filed: Dec. 19, 1979

[51] Int. Cl.³ .................. A01N 57/14; C07F 9/38
[52] U.S. Cl. ..................... 71/86; 260/502.4 R
[58] Field of Search .............. 71/86; 260/502.4 R

[56] References Cited

U.S. PATENT DOCUMENTS

| | | | |
|---|---|---|---|
| 3,223,514 | 12/1965 | Gradstern | 71/86 |
| 3,338,702 | 8/1967 | Newcomer, et al. | 71/86 |
| 3,826,641 | 7/1974 | Porter | 71/86 |

*Primary Examiner*—Anton H. Sutto
*Attorney, Agent, or Firm*—Dietmar H. Olesch; Robert J. Schwarz

[57] ABSTRACT

This invention discloses a method of increasing the recoverable sugar contained in sugar cane which comprises contacting the sugar cane plant with an effective amount of a compound of the formula

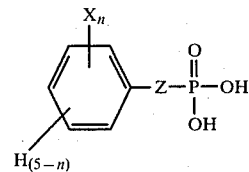

wherein X is selected from the group consisting of alkyl, halogen, trifluoromethyl and alkoxy; n is an integer from 0 to 5; and Z is a straight or branched alkylene group containing from 1 to 5 carbon atoms.

7 Claims, No Drawings

METHOD OF INCREASING THE YIELDS OF SUGAR CANE WITH PHOSPHONIC ACIDS

This invention relates to a method of increasing the yield of sugar obtained from sugar cane and more particularly relates to a method of increasing the recoverable sugar in sugar cane by treating the sugar cane plant during its maturation with certain phenylalkylenephosphonic acids.

A variety of plant growth regulators, stimulants and promoters have been tried in the past in attempts to increase the yields of cultivated crops. These attempts have met with varying success but have generally attained limited commercial significance. One particular crop which has been given increased attention for the purpose of augmenting yields is sugar cane. Accordingly, it is an object of the present invention to provide a new method of increasing the yield of sugar obtained from sugar cane.

Surprisingly, it has been found that the recovery of sugar from sugar cane can be substantially increased through the use of certain phosphonic acids. Thus, one embodiment of the present invention resides in a method of increasing the recoverable sugar contained in sugar cane which comprises contacting the sugar cane plant with an effective amount of a compound of the formula

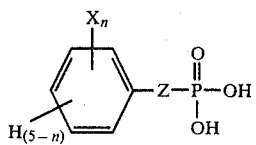

wherein X is selected from the group consisting of alkyl, halogen, trifluoromethyl and alkoxy; n is an integer from 0 to 5; and Z is a straight or branched alkylene group containing from one to five carbon atoms.

In a preferred embodiment of the present invention, X is selected from the group consisting of lower alkyl, halogen, trifluoromethyl, lower alkoxy and nitro. The term lower as used herein designates a straight or branched carbon chain of 1 to 6 carbon atoms.

The compounds of the present invention dexcribed in formula I are generally known in the art but when not readily available they can be readily prepared by hydrolyzing a compound of the formula

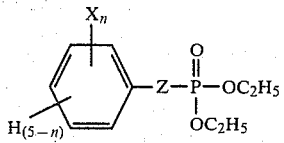

wherein X, n and Z are as heretofore described, with hydrochloric acid. This reaction can be effected by heating the compound of Formula II with concentrated hydrochloric acid at the reflux temperature of the mixture for a period of from about 1 to about 6 hours. After this time the mixture is cooled to yield the desired product as a solid product. This product can then be further purified, if desired, by conventional techniques such as washing, recrystallizing and the like.

The compounds of Formula II can be prepared by reacting triethylphosphite with a compound of the formula

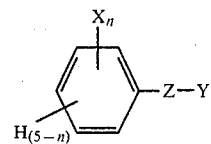

wherein X, n and Z are as heretofore described and Y is chlorine or bromine. This reaction can be effected by combining about equimolar amounts of the reactants in a suitable reaction vessel and heating the mixture at a temperature ranging from about 100° to about 300° C. for a period of from about one-half to about 4 hours. After this time the mixture can be cooled and distilled under reduced pressure to remove ethyl chloride or bromide and to yield the desired product.

Exemplary compounds of Formula III, useful in preparing the compounds of the present invention, are benzyl chloride, 2-methylbenzyl chloride, 4-methylbenzyl chloride, 2,4-dimethylbenzyl chloride, 4-propylbenzyl chloride, 4-t-butylbenzyl chloride, 4-hexylbenzyl chloride, 2-chlorobenzyl chloride, 4-chlorobenzyl chloride, 2,4-dichlorobenzyl chloride, 4-bromobenzyl chloride, 3,4-dibromobenzyl chloride, 4-iodobenzyl chloride, 4-fluorobenzyl chloride, 4-trifluoromethylbenzyl chloride, 2-methoxybenzyl chloride, 3-ethoxybenzyl chloride, 4-propoxybenzyl chloride, 2-methoxy-3,6-dichlorobenzyl chloride, 2,6-dinitrobenzyl chloride, $\beta$-chlorophenethyl, $\beta$-3,4-trichlorophenethyl, 1-chloro-3-phenylpropane, 1-chloro-2-methyl-3-phenylpropane, 1-chloro-2,2-dimethyl-3-phenylpropane and the like.

The manner in which the compounds of the present invention can be prepared is more specifically illustrated in the following examples.

EXAMPLE 1

Preparation of O,O-Diethyl 2,6-Dichlorobenzylphosphonate 2,6-Dichlorobenzyl chloride (1200 grams) and triethyl phosphate (1115 grams) were charged into a glass reaction vessel equipped with a mechanical stirrer, thermometer and reflux condenser. The reaction mixture was heated for a period of 60 minutes until the temperature reached 195° C. After this time the mixture was cooled and thereafter distilled under reduced pressure to yield the desired product O,O-diethyl 2,6-dichlorobenzylphosphonate having a boiling point of 158° to 168° C. at 0.4–0.6 mm of Hg pressure.

EXAMPLE 2

Preparation of 2,6-Dichlorobenzylphosphonic Acid

O,O-Diethyl 2,6-dichlorobenzylphosphonate (1794 grams) and concentrated hydrochloric acid (2 l) were charged into a glass reaction vessel equipped with a mechanical stirrer, thermometer and reflux condenser. The reaction mixture was heated at reflux for a period of 16 hours. The mixture was then cooled in the formation of a solid product. This product was recovered by filtration was washed with water and dried to yield the desired product 2,6-dichlorobenzylphosphonic acid having a melt point of 211° to 218° C.

Additional compounds within the scope of the present invention useful for increasing the yield of sugar obtained from sugar cane include but are not limited to the following:
4-chlorobenzylphosphonic acid
2-methylbenzylphosphonic acid
2-bromobenzylphosphonic acid
4-methylbenzylphosphonic acid
4-fluorobenzylphosphonic acid
2-fluorobenzylphosphonic acid
3-chlorobenzylphosphonic acid
3,4-dichlorobenzylphosphonic acid
2-chlorobenzylphosphonic acid
3-fluorobenzylphosphonic acid
3-bromobenzylphosphonic acid
3-methylbenzylphosphonic acid
4-ethylbenzylphosphonic acid
4-iodobenzylphosphonic acid
4-propylbenzylphosphonic acid
3-hexylbenzylphosphonic acid
4-trifluorobenzylphosphonic acid
2-methoxybenzylphosphonic acid
3-ethoxybenzylphosphonic acid
4-hexyloxybenzylphosphonic acid
2-methyl-3,4-dichlorobenzylphosphonic acid
2,4,6-trimethylbenzylphosphonic acid
4-chlorophenethylphosphoric acid
3-(2,6-dichlorophenyl)propylphosphoric acid
2-methyl-4(3-bromophenyl)butylphosphoric acid To effect the method of this invention, sugar cane is treated at a late stage of development. This treatment is carried out during that stage of development of the sugar cane wherein most of the sugar formation takes place. Thus, under normal growing conditions and common cultivation practices the active compounds of this invention can be applied to the sugar cane during the period of from about 2 to about 10 weeks before harvesting.

The amount of active compound required to effectively increase the recoverable sugar from sugar cane can vary somewhat depending on such factors as the time of application, the weather, crop density, method of application and the like. Generally, an amount of at least 0.1 pounds per acre and preferably an amount of from 0.1 pounds per acre to about 10 pounds per acre can be used. While an amount greater than those mentioned can be used, they will not result in an advantage that would warrant their expense and are therefore, not practical.

For practical use in treating sugar cane the active compound of this invention is generally incorporated into compositions or formulations which comprise an inert carrier and an effective amount of the compound. The compositions enable the active compound to be conveniently applied to the sugar cane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound according to this invention and as the inert carrier, a solvent and an emulsifier. Such emulsifiable concentrates can be extended with water and/or oil to any desired concentration of active compound for application as sprays to the sugar cane. The emulsifier most commonly used in these concentrates are nonionic or mixtures of nonionic with anionic surface-active agents. With the use of some emulsifier systems an inverted emulsion (water-in-oil) can be prepared.

Typical formulations according to the present invention useful for increasing the recoverable sugar in sugar cane are illustrated in the following examples wherein the quantities are given in parts by weight.

EXAMPLE 3

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| Product of Example 2 | 25 |
|---|---|
| Sodium lauryl sulfate | 2 |
| Sodium lignin sulfate | 3 |
| Kerosene | 70 |

EXAMPLE 4

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugar cane.

| Product of Example 2 | 50 |
|---|---|
| Fuller's earth | 47 |
| Sodium lauryl sulfate | 2.5 |
| Methyl cellulose | 0.5 |

EXAMPLE 5

Preparation of a Dust

The following ingredients are mixed thoroughly and are then ground to an average particle size of less than about 50 microns to give a dust suitable for application with conventional dusting equipment.

| Product of Example 2 | 10 |
|---|---|
| Powdered talc | 90 |

The effectiveness of the compounds of this invention for increasing the recoverable sugar from sugar cane was demonstrated in a field test by applying a solution in acetone diluted for application to the various indicated application rates. The test compound was applied at each rate on the spindle area of each of 20 stalks of sugar cane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

The top 14 joints of the treated cane as well as those of the controls were removed, combined and analyzed for juice purity and pol percent cane, following the "press method" developed and described by T. Tanimoto, Hawaiian Planters Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugar cane.

The effectiveness of the compounds of this invention for increasing the yield of sugar obtained from sugar cane is demonstrated by the data set out in the following Tables. Each table represents a separate experiment conducted at a different time. The cane was harvested 8 weeks after application of the test compound. The test compounds in the tables are coded for brevity as follows:

| Compound No. | Chemical Identity |
|---|---|
| 1 | 2,6-dichlorobenzylphosphonic acid |
| 2 | 4-chlorobenzylphosphonic acid |
| 3 | 2-methylbenzylphosponic acid |
| 4 | 2-bromobenzylphosphonic acid |
| 5 | 4-methylbenzylphosphonic acid |
| 6 | 4-fluorobenzylphosphonic acid |
| 7 | 2-fluorobenzylphosphonic acid |
| 8 | 3-chlorobenzylphosphonic acid |
| 9 | 3,4-dichlorobenzylphosphonic acid |
| 10 | 3-bromobenzylphosphonic acid |
| 11 | 3-fluorobenzylphosphonic acid |
| 12 | 2-chlorobenzylphosphonic acid |
| 13 | 3-methylbenzylphosphonic acid |
| 14 | 4-bromobenzylphosphonic acid |

TABLE I

| Test Compound | Rate Lbs./Acre | Juice Purity | Pol % Cane |
|---|---|---|---|
| 1 | 4 | 89.72 | 14.20 |
| 2 | 4 | 89.05 | 13.52 |
| 3 | 4 | 83.82 | 11.34 |
| Control | 0 | 83.90 | 11.07 |

TABLE II

| Test Compound | Rate Lbs./Acre | Juice Purity | Pol % Cane |
|---|---|---|---|
| 1 | 1 | 80.33 | 11.29 |
| 2 | 1 | 77.52 | 10.17 |
| Control | 0 | 89.55 | 9.20 |

TABLE III

| Test Compound | Rate Lbs./Acre | Juice Purity | Pol % Cane |
|---|---|---|---|
| 2 | 1 | 86.36 | 13.36 |
| 1 | 1 | 82.21 | 11.41 |
| 4 | 1 | 81.87 | 11.18 |
| 5 | 1 | 80.11 | 10.81 |
| 6 | 1 | 80.26 | 10.80 |

TABLE III-continued

| Test Compound | Rate Lbs./Acre | Juice Purity | Pol % Cane |
|---|---|---|---|
| 7 | 1 | 80.33 | 10.56 |
| 8 | 1 | 78.71 | 10.37 |
| 9 | 1 | 78.24 | 10.25 |
| Control | 0 | 72.90 | 8.32 |

TABLE IV

| Test Compound | Rate Lbs./Acre | Juice Purity | Pol % Cane |
|---|---|---|---|
| 10 | 1 | 87.89 | 14.48 |
| 11 | 1 | 88.39 | 14.44 |
| 12 | 1 | 86.81 | 13.54 |
| 13 | 1 | 87.33 | 13.49 |
| 14 | 1 | 85.30 | 12.61 |
| 1 | 1 | 78.67 | 10.46 |
| Control | 0 | 84.16 | 12.54 |

I claim:

1. A method of increasing the recoverable sugar contained in sugar cane which comprises contacting the sugar plant during the period of from about 2 to about 10 weeks before harvesting with an effective amount of a compound of the formula

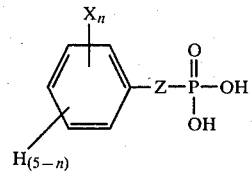

wherein X is selected from the group consisting of lower alkyl, halogen, trifluoromethyl and lower alkoxy; n is an integer from 0 to 2 provided that when n is 2 the X substituents are in the 2, 5 or 2, 6 positions; and Z is a straight or branched alkylene group containing from 1 to 5 carbon atoms.

2. The method of claim 1 wherein the sugar cane is contacted with about 0.1 to about 10 pounds per acre of said compound.

3. The method of claim 2 wherein said compound is 2,6-dichlorobenzylphosphonic acid.

4. The method of claim 2 wherein said compound is 4-chlorobenzylphosphonic acid.

5. The method of claim 2 wherein said compound is 2-bromobenzylphosphonic acid.

6. The method of claim 2 wherein said compound is 3-bromobenzylphosphonic acid.

7. The method of claim 2 wherein said compound is 3-fluorobenzylphosphonic acid.

* * * * *